United States Patent [19]
Deck et al.

[11] Patent Number: 6,114,545
[45] Date of Patent: Sep. 5, 2000

[54] INHIBITORS OF CHOLESTEROL ESTERASE

[75] Inventors: Lorraine Deck; David L. Vander Jagt, both of Albuquerque, N. Mex.

[73] Assignee: University of New Mexico, Albuquerque, N. Mex.

[21] Appl. No.: 09/464,194

[22] Filed: Dec. 16, 1999

Related U.S. Application Data

[62] Division of application No. 09/291,990, Apr. 15, 1999, Pat. No. 6,034,255, which is a division of application No. 09/060,250, Apr. 15, 1998, Pat. No. 5,942,631
[60] Provisional application No. 60/041,988, Apr. 16, 1997.
[51] Int. Cl.$^7$ ..................... C07D 307/83; C07D 311/20; C07D 311/74
[52] U.S. Cl. ............................................. 549/283; 549/302
[58] Field of Search ....................... 549/283, 302

[56] References Cited

U.S. PATENT DOCUMENTS

| | | | |
|---|---|---|---|
| 4,749,798 | 6/1988 | Gandolfi et al. | 549/283 |
| 5,464,824 | 11/1995 | Gaudin | 549/302 |

*Primary Examiner*—Ba K. Trinh
*Attorney, Agent, or Firm*—Jagtiani & Associates

[57] ABSTRACT

The present invention provides novel haloenol lactones that are effective as active site inhibitors of cholesterol esterase. By inhibiting cholesterol esterase the inhibitors of the present invention provide a new approach to the treatment of hypercholesterolemia through limiting the bioavailability of dietary cholesterol.

7 Claims, 4 Drawing Sheets

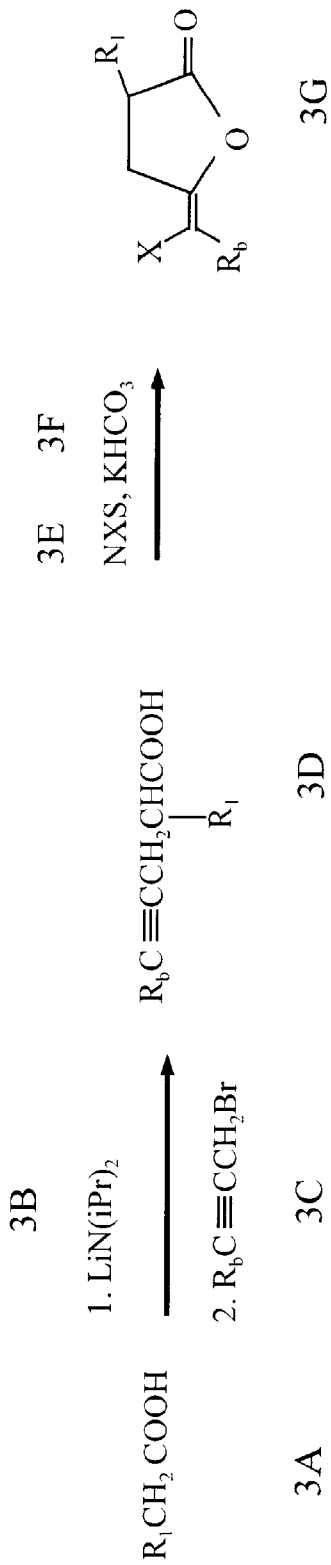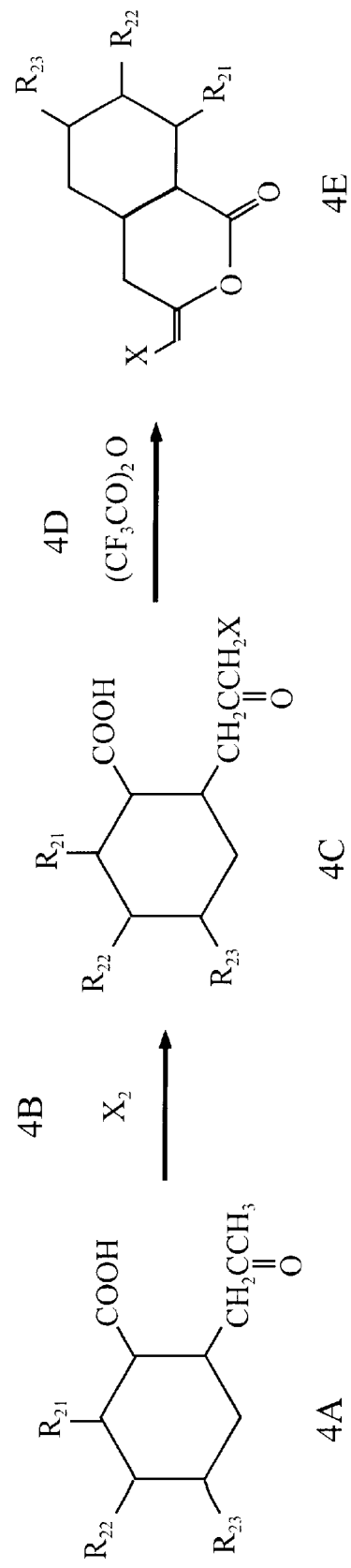

INHIBITORS OF CHOLESTEROL ESTERASE

RELATED APPLICATION

This application is a division of U.S. Ser. No. 09/291,990 filed Apr. 15, 1999, now U.S. Pat. No. 6,034,255, which is a division of U.S. Ser. No. 09/060,250 filed Apr. 15, 1998, now U.S. Pat. No. 5,942,631, which is based on U.S. Provisional Patent Application No. 60/041,988 filed Apr. 16, 1997, the entire disclosure and contents of which is hereby incorporated by reference.

BACKGROUND OF THE INVENTION

1. Field of the Invention

The present invention relates to inhibitors of cholesterol esterase.

2. Description of the Prior Art

Primary hypercholesterolemia is an established risk factor of atherosclerosis and coronary heart disease (CHD). Epidemiological data indicate a positive relationship between serum LDL-cholesterol and CHD which is the leading cause of death in both men and women in the United States. Clinical trials with cholesterol-lowering regimens are beneficial in the prevention of CHD morbidity and mortality. A variety of regimens have been used to lower serum cholesterol including diet restriction, nicotinic acid, bile acid sequestrants, and HMGCoA reductase inhibitors. Reductase inhibitors have become widely used in recent years. Although generally well tolerated and effective, side effects have been reported in up to 4% of participants in controlled trials, including increases in serum levels of hepatic headache, and sleep disorders. With prolonged use, other side effects have been reported including depression, sensorimotor neuropathy and eczema. Alternative therapies are needed, especially for populations that cannot tolerate reductase inhibitors.

SUMMARY OF THE INVENTION

It is an object of the present invention to provide active site inhibitors of cholesterol esterase for prevention of the hydrolysis of the cholesterol ester. By inhibiting cholesterol esterase the inhibitors of the present invention provide a new approach to the treatment of hypercholesterolemia through limiting the bioavailability of dietary cholesterol.

In one embodiment, the present invention provides a compound comprising:

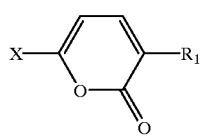

wherein:

X=Cl, Br or I; and $R_1$ is a member of the group consisting of :

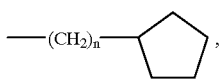

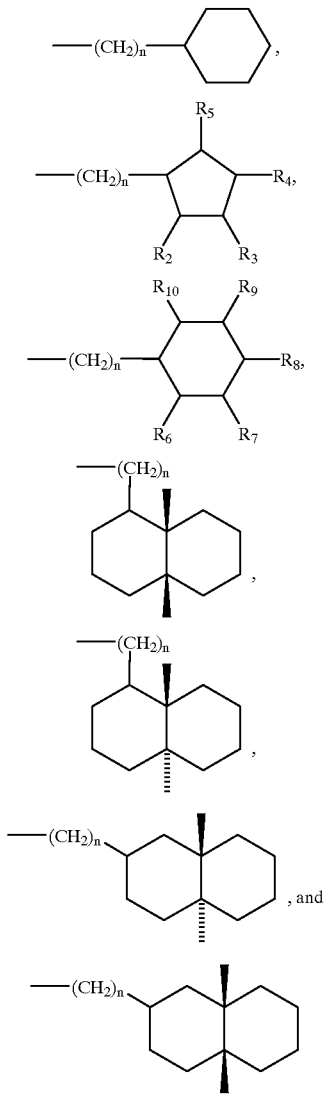

wherein:

n=0 to 8; and $R_2$, $R_3$, $R_4$, $R_5$, $R_6$, $R_7$, $R_8$, $R_9$, and $R_{10}$=H, $C_{1-8}$ alkyl, $C_{3-8}$ cycloalkyl, $C_{2-8}$ alkenyl, or $C_{2-4}$ alkynyl.

In a second embodiment, the present invention provides a compound comprising:

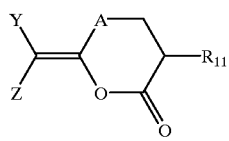

wherein

A=$-(CH_2)_p-$ where p=0 or 1;

Y=H or $C_{1-8}$ alkyl when Z=Cl, Br, or I and Y=Cl, Br, or I when Z=H or $C_{1-8}$ alkyl; and $R_{11}$ is a member of the group consisting of:

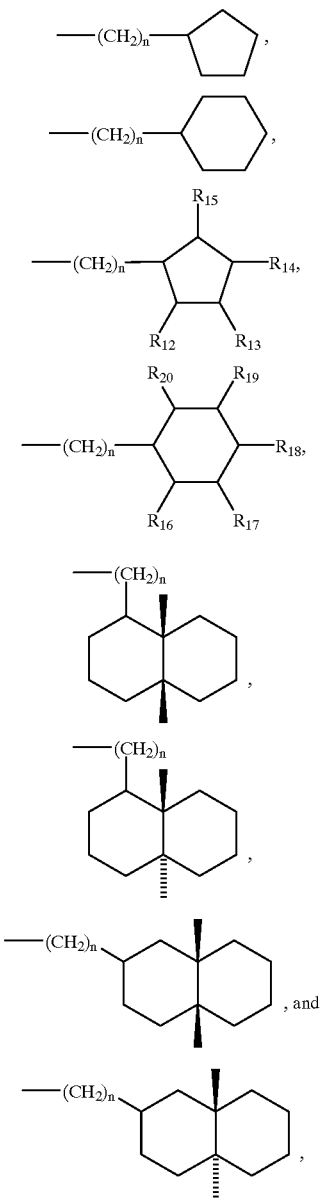

wherein n=0 to 8; and $R_{12}$, $R_{13}$, $R_{14}$, $R_{15}$, $R_{16}$, $R_{17}$, $R_{18}$, $R_{19}$, and $R_{20}$=H, $C_{1-8}$ alkyl, $C_{3-8}$ cycloalkyl, $C_{2-8}$ alkenyl, or $C_{2-8}$ alkynyl.

In a third embodiment, the present invention provides a compound comprising:

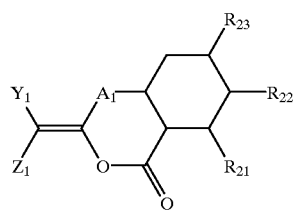

wherein $A_1$=—$(CH_2)_q$— where q=0 or 1;

$Y_1$=H or $C_{1-8}$ alkyl when $Z_1$=Cl, Br, or I and $Y_1$=Cl, Br, or I when $Z_1$=H or $C_{1-8}$ alkyl; and $R_{21}$, $R_{22}$, $R_{23}$=H, $C_{1-8}$ alkyl, $C_{3-8}$ cycloalkyl, $C_{2-8}$ alkenyl, or $C_{2-8}$ alkynyl.

Other objects and features of the present invention will be apparent from the following detailed description of the preferred embodiments.

BRIEF DESCRIPTION OF THE DRAWINGS

The invention will be described in conjunction with the accompanying drawings, in which:

FIG. 3 illustrates a third method for forming compounds of the present invention;

FIG. 4 illustrates a fourth method for forming compounds of the present invention;

DETAILED DESCRIPTION OF THE PREFERRED EMBODIMENTS

Definitions

Figure 1:
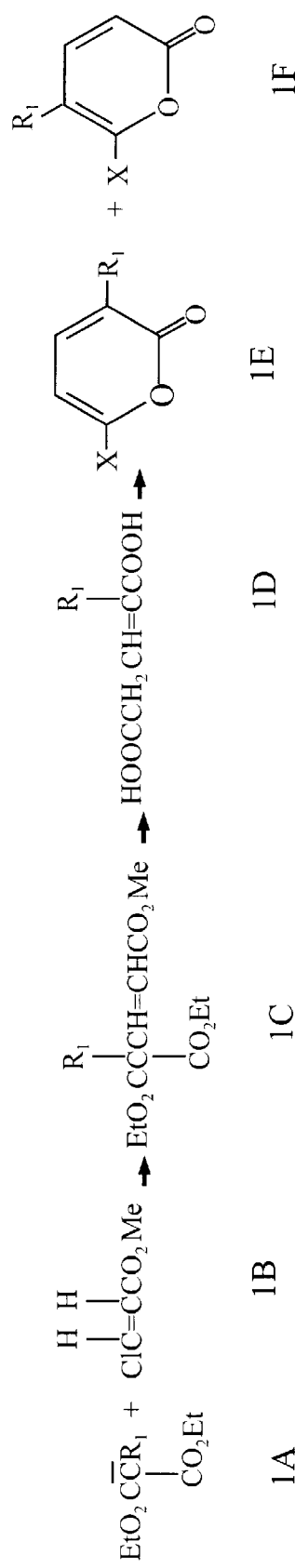
FIG. 1 illustrates one method for forming compounds of the present invention.

The term "$C_{1-8}$ alkyl" refers to a straight or branched chain alkyl moiety having one ot eight carbon atoms including for example, methyl, ethyl, propyl, isopropyl, butyl, sec-butyl, isobutyl, pentyl, dimethyl-propyl, hexyl, and octyl, and cognate terms (such as "$C_{1-8}$ alkoxy") are to be construed accordingly. Similarly, the term "$C_{1-5}$ alkyl" refers to a straight or branched chain alkyl moiety having one to five carbon atoms (such as methyl or ethyl).

The term "$C_{1-8}$ cycloalkyl" refers to a saturated alicyclic moiety having from 3 to 8 carbon atoms arranges in a ring and includes, for example, cyclopropyl, cyclobutyl, cyclopentyl, and cyclooctyl.

The term "$C_{2-8}$ alkenyl" refers to a straight or branched chain alkyl moiety having one to eight carbon atoms and having in addition at least one double bond of either E or Z stereochemistry where applicable. This term would include, for example, vinyl, 1-propenyl, 1- and 2-butenyl and 2-methyl-2-propenyl.

The term "$C_{2-8}$ alkynyl" refers to a straight or branched chain alkyl moiety having one to eight carbon atoms and having in addition at least one triple bond. This term would include, for example, propargyl, and 1- and 2-butynyl.

For the purposes of the present invention, including the accompanying drawing figures, the possible values for the radicals $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, and $R_{23}$ are set forth above in the summary of the invention section.

For the purposes of the present invention, including the accompanying drawing figures, the letter "X" represents any one of the halide radicals Cl, Br and I and "$X_2$" represents any one of $Cl_2$, $Br_2$ and $I_2$.

Description

Artherosclerotic heart disease is correlated to serum cholesterol levels. Therefore, a treatment which decreases the amount of dietary cholesterol absorbed from the intestine should also reduce a person's susceptibility to atherosclerotic heart disease.

The compounds of the present invention act as cholesterol esterase (CE) inhibitors, that is they prevent CE from hydrolyzing dietary cholesterol esters in the intestines. The compounds of the present invention have structures which allow them to enter the active site of CE, a serine esterase, and bind covalently to certain residues. This results in a permanent inactivation of the enzyme. The compounds of the present invention combine structural features of known good inhibitors of serine esterases and the structural features of a known potent irreversible inhibitor of CE.

Dietary cholesterol is comprised of free and esterified cholesterol, the ratio depending upon the dietary source. In diets rich in meats, up to 75% of cholesterol is esterified. Hydrolysis of cholesterol ester in the lumen of the small intestine is catalyzed by cholesterol esterase (CE) which liberates free cholesterol. Free cholesterol mixes with cholesterol contained in bile secretions to form the pool of cholesterol which is capable of being absorbed. Due to the low solubility of cholesterol, solubilization of cholesterol by bile salts into micelles is essential. In addition, transport proteins are required to deliver cholesterol from micelles to the enterocytes for absorption. CE provides both the hydrolytic activity for hydrolysis of cholesterol ester and the transport function for delivery of cholesterol from micelles to enterocytes. Esterification of cholesterol within the enterocyte also utilizes CE which can catalyze the reverse reaction under certain conditions. CE within the enterocyte is immunochemically related to pancreatic CE. Given the essential role of CE in hydrolysis of cholesterol esters and in cholesterol absorption, the present invention's active site inhibitors of CE are effective in reducing the bioavailability of dietary cholesterol.

The catalytic mechanism of pancreatic CE resembles that of serine proteases such as trypsin and serine esterases such as acetylcholine esterase. Sequence comparisons indicate that S194, H435 and D79 comprise the active site triad of serine, histidine and aspartic acid in pancreatic CE, corresponding to S195, H57 and D102 in trypsin. The importance of these residues in CE has been demonstrated by site directed mutagenesis studies by DiPersio et al. in "Site-directed mutagenesis of an essential histidine residue in pancreatic cholesterol esterase," *J. Biol. Chem.*, 266, 4033–4036 (1991).

The feasibility of using a active site inhibitor to reduce cholesterol absorption has been reported by Bailey et al in. "Inhibition of dietary cholesterol ester absorption by 3-BCP, a suicide inhibitor of cholesterol esterase," *Biochem. Soc. Trans.*, 23, 408S (1995). Intragastric administration of a single dose of 3-benzyl-6-chloropyrone to rats simultaneous with feeding of cholesterol ester resulted in a 60% drop in cholesterol absorption, which resulted from a 63% inactivation of lumenal CE activity. In vitro CE was inactivated by this pyrone with a half life of 100 seconds. 3-Benzyl-6-chloropyrone is a prototype haloenol lactone that has been developed as a suicide inhibitor of chymotrypsin, although it is not highly selective as described in Daniels et al. in "Haloenol lactones. Potent enzyme-activated irreversible inhibitors for α-chymotrypsin," *J. Biol. Chem.*, 250, 15046–15053 (1983) (Suicide inhibitors, also called suicide substrates, require catalytic activation to a form that irreversibly modifies the enzyme). The compounds of the present invention improve on existing haloeonol lactone suicide inhibitors by being selective for CE.

One method for synthesizing compounds of the present invention is Scheme 1 illustrated in FIG. 1. An appropriately substituted diethylmalonate sodium salt (1A) is heated with a cis-2-chloroacrylate (1B) to give a triester compound (1C). Saponification and decarboxylation of the triester compound (1C) produces a substituted glutaconic acid (1D) which is often present as a mixture of the E and Z isomers. Cyclization is then performed using an acetyl halide cyclization agent (such as acetyl chloride or acetyl bromide) to give the 3-substituted 6-halopyrone (1E) and 5-substituted 6-halopyrone (1F). The 3-substituted 6-halopyrone of the invention (1E) is then separated form the other isomer and purified using conventional column chromatography techniques. The method of scheme 1 is similar to a procedure described by Boulanger and Katzenellenbogen in "Structure Activity Study of 6-Substituted 2-Pyranones as Inactivators of α-chymotrypsin" in *J. Med. Chem.*, 29 1159–1163 (1986).

Figure 2:
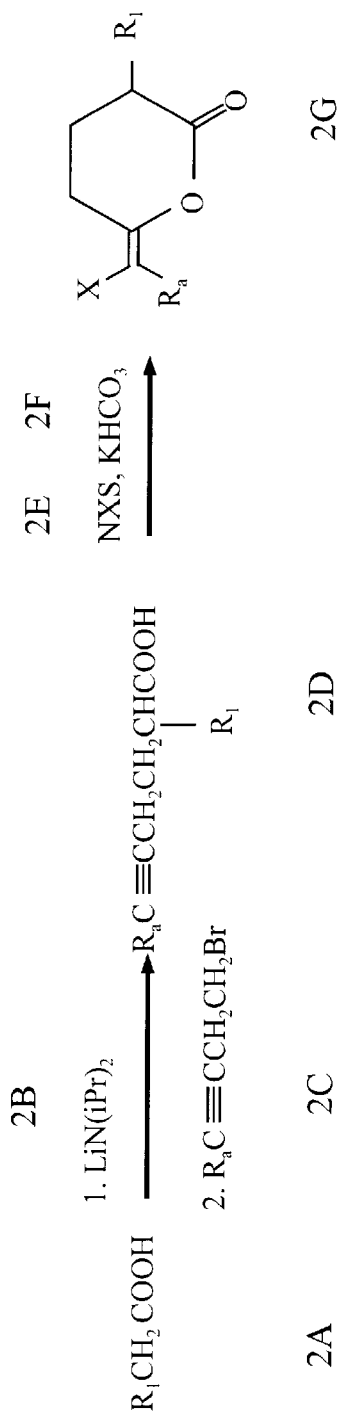
FIG. 2 illustrates a second method for forming compounds of the present invention.

A second method for synthesizing compounds of the present invention is Scheme 2 illustrated in FIG. 2. Cyclohexylacetic acid (2A) is reacted with two moles of lithium diisopropyl amide (2B) followed by alkylation with a 4-alkyl-1-bromo-3-butyne (2C) to produce an acetylenic acid intermediate (2D) (Where $R_n=C_{1-8}$ alkyl). Halolactone compounds of the present invention (2G) are then produced by halolactonization of the acetylenic acid intermediate (2D) with an N-halosuccinimide (NXS; 2E) and potassium bicarbonate (2F). Depending on the desired halide substituent (X) in the halolactone, the N-halosuccinimide (2E) can be N-bromosuccinimide, N-chlorosuccinimide or N-iodosuccinimide.

A third method for synthesizing compounds of the present invention is Scheme 3 illustrated in FIG. 3. Cyclohexylacetic acid (3A) is reacted with two moles of lithium diisopropyl amide (3B) followed by alkylation with a 3-alkyl-1-bromo-2-propyne (3C) to produce an acetylenic acid intermediate (3D) (Where $R_b=C_{1-8}$ alkyl). Halolactone compounds of the present invention (3G) are then produced by halolactonization of the acetylenic acid intermediate (3D) with an N-halosuccinimide (NXS; 3E) and potassium bicarbonate (3F). Depending on the desired halide substituent (X) in the halolactone, the N-halosuccinimide (3E) can be N-bromosuccinimide, N-chlorosuccinimide or N-iodosuccinimide.

A fourth method for synthesizing compounds of the present invention is Scheme 4 illustrated in FIG. 4. 2-(2-Oxopropyl)cyclohexanecarboxylic acid (4A) is reacted with a halogen $X_2$ (4B) to produce a halo keto acid intermediate (4C). Depending on the desired halide substituent in the halolactone (4E), $X_2$ can be chlorine, bromine or iodine. Pyridinium tribromide can be used as the source of bromine. Halolactone compounds of the present invention (4E) are then produced by halolactonization of the intermediate (4C) with trifluoroacetic acid anhydride (4D).

Figure 5:
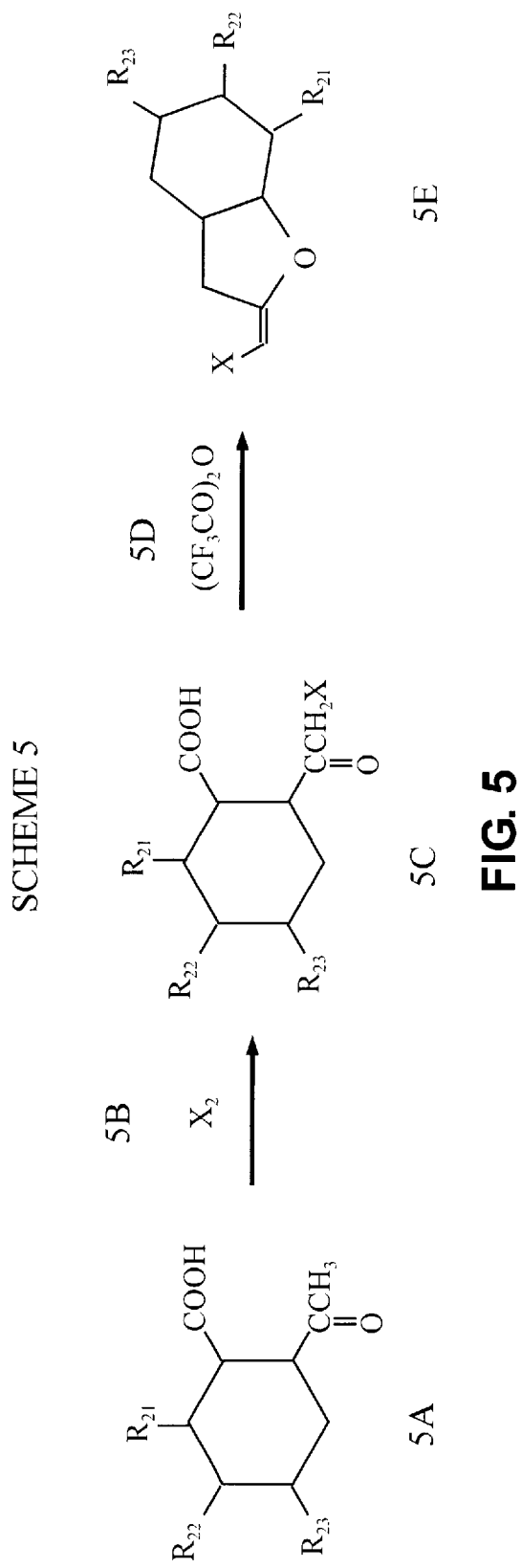
FIG. 5 illustrates a fifth method for forming compounds of the present invention.

A fifth method for synthesizing compounds of the present invention is Scheme 5 illustrated in FIG. 5. 2-Acetylcyclohexanecarboxylic acid (5A) is reacted with a halogen $X_2$ (5B) to produce a halo keto acid intermediate (5C). Depending on the desired halide substituent in the halolactone (5E). $X_2$ can be chlorine, bromine or iodine. Pyridinium tribromide can be used as the source of bromine. Halolactone compounds of the present invention (5E) are then produced by halolactonization of the intermediate (5C) with trifluoroacetic acid anhydride (5D).

The synthesis methods of scheme 2 and scheme 3 stereospecifically produce the E isomers 2G and 3G. The Z isomers of these compounds can be produced using a method similar to that described in Dai and Katzenellenbogen, "Stereoselective Z- and E- Bromo Enol Lactonization of Alkynoic Acids" in *J. Org. Chem.*, 56, 6893–6896 (1991). For example, treating the silver salt of compound 2D with a halogen X in acetonitrile can be used to provide the following Z isomer compound of the present invention 2H:

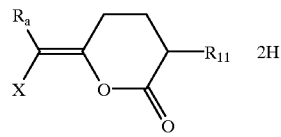

Similarly, treating the silver salts of compounds 3D, 4D, and 5D can be used to produce the following Z isomer compounds of the present invention 3H, 4H and 5H, respectively:

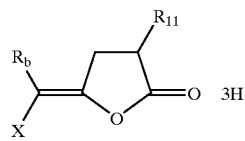

EXAMPLE 1

A 3-substituted 6-chloropyrone of the invention was prepared according to Scheme 1, wherein X=Cl, $R_1=$

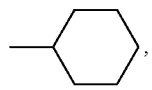

and acetyl chloride was used as a cyclization agent. NMR analysis of this compound provided the following results: H'NMR (CDCl$_3$): 7.02 (d, 1H), 6.16 (d, 1H). 2.59 (m, 1H). 1.90–1.14 (m, 10H).

EXAMPLE 2

A 3-substituted 6-chloropyrone of the invention was prepared according to Scheme 1, wherein X=Cl, $R_1=$

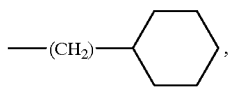

and acetyl chloride was used as a cyclization agent. NMR analysis of this compound provided the following results: H'NMR (CDCl$_3$): 7.05 (d, 1H), 6.16 (d, 1H), 2.45 (d, 2H), 1.80–0.81 (m, 11H).

EXAMPLE 3

A 3-substituted 6-chloropyrone of the invention was prepared according to Scheme 1, wherein X=Cl, $R_1=$

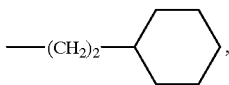

and acetyl chloride was used as a cyclization agent. NMR analysis of this compound provided the following results: H'NMR (CDCl$_3$): 7.02 (d, 1H), 6.11 (d, 1H), 2.39 (t, 2H), 1.72–0.85 (m, 13H).

EXAMPLE 4

A 3-substituted 6-chloropyrone of the invention was prepared according to Scheme 1, wherein X=Cl, $R_1=$

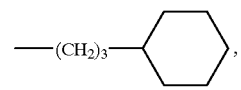

and acetyl chloride was used as a cyclization agent. NMR analysis of this compound provided the following results: H'NMR (CDCl$_3$): 7.05 (d, 1H), 6.15 (d, 1H), 2.40 (t, 2H), 1.71–0.80 (m, 15H).

EXAMPLE 5

A 3-substituted 6-chloropyrone of the invention was prepared according to Scheme 1, wherein X=Cl, $R_1=$

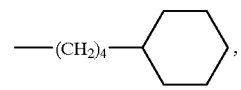

and acetyl chloride was used as a cyclization agent.

EXAMPLE 6

A 3-substituted 6-chloropyrone of the invention was prepared according to Scheme 1, wherein X=Cl, $R_1=$

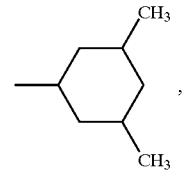

and acetyl chloride was used as a cyclization agent.

EXAMPLE 7

A 3-substituted 6-chloropyrone of the invention was prepared according to Scheme 1, wherein X=Cl, $R_1=$

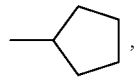

and acetyl chloride was used as a cyclization agent. NMR analysis of this compound provided the following results: H'NMR (CDCl$_3$): 7.09 (d, 1H), 6.16 (d, 1H), 2.95 (pent, 1H), 2.00–1.46 (m8H).

EXAMPLE 8

A 3-substituted 6-chloropyrone of the invention was prepared according to Scheme 1, wherein X=Cl, $R_1=$

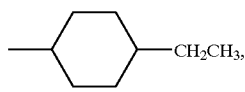

and acetyl chloride was used as a cyclization agent.

EXAMPLE 9

A compound of the present invention is prepared according to Scheme 2, wherein X=Br, $R_1$=CH$_6$H$_{11}$, and n-bromosuccinimide is used as a cyclization agent.

EXAMPLE 10

A compound of the present invention is prepared according to Scheme 2, wherein X=Br, $R_1$=CH$_7$H$_{13}$, and n-bromosuccinimide is used as a cyclization agent.

EXAMPLE 11

A compound of the present invention is prepared according to Scheme 2, wherein X=Br, $R_1$=CH$_8$H$_{15}$, and n-bromosuccinimide is used as a cyclization agent.

EXAMPLE 12

A compound of the present invention is prepared according to Scheme 3, wherein X=Br, $R_1$=CH$_6$H$_{11}$, and n-bromosuccinimide is used as a cyclization agent.

EXAMPLE 13

A compound of the present invention is prepared according to Scheme 3, wherein X=Br, $R_1$=CH$_7$H$_{13}$, and n-bromosuccinimide is used as a cyclization agent.

EXAMPLE 14

A compound of the present invention is prepared according to Scheme 3, wherein X=Br, $R_1$=CH$_8$H$_{15}$, and n-bromosuccinimide is used as a cyclization agent.

Figure 6:
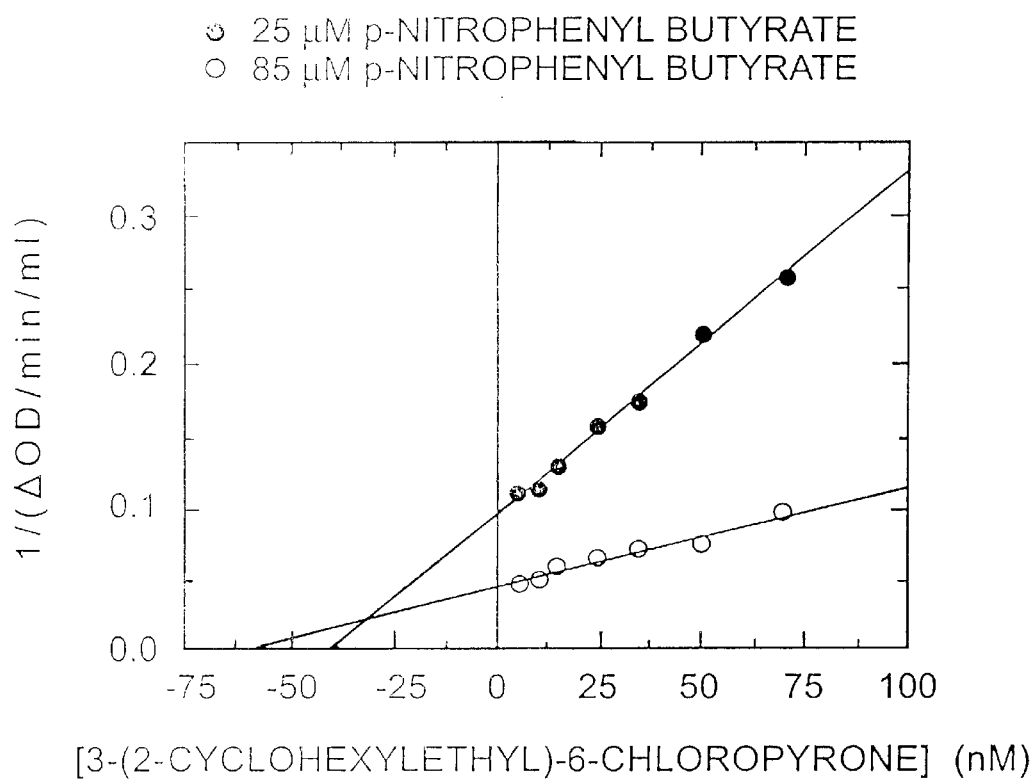
FIG. 6 is a graph showing the inhibition of cholesterol esterase by a compound of the present invention.

Kinet c inhibition studies of the compounds of Examples 1, 2, 3 and 4 revealed that all four of the compounds are potent inhibitors of CE. Representative data is shown in FIG. 6 for inhibition of CE by 3-(2-cyclohexylethyl)-6-chloropyrone, the compound of Example 3. The data were analyzed by Dixon plots. As shown in FIG. 6, the plot of 1/V v [I] at two different fixed concentrations of the substrate p-nitrophenylbutyrate intersect above the x-axis, indicative of competitive inhibition. The calculated $K_i$=30 ηM. However, a value of 30 ηM corresponds to one half of the concentration of CE used in this assay, suggesting that the actual $K_i$<<30 ηM.

In inhibition studies with high affinity inhibitors under conditions where the concentration of enzyme used in the assay exceeds the concentration of the inhibitor, the $K_i$ obtained is an apparent $K_i$ corresponding to [E]/2. Therefore, clearly, the compounds of the present invention are potent inhibitors of CE.

The compounds of the present invention are also highly selective for CE, unlike 3-substituted 6-chloropyrones such as 3-benzyl-6-chloropyrone where the 3-substituent includes an aromatic ring. For example, the compound of Example 3 has been found to inhibit chymotrypsin with $K_i$=50 μM compared to $K_i$<<30 ηM for inhibition of CE. Thus, the compounds of the present invention which have a saturated ring as part of the 3-substituent provide tremendous selectively when compared to compounds where the 3-substituent includes an aromatic ring.

What is claimed is:

1. A compound comprising:

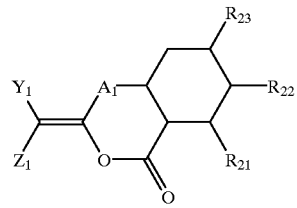

wherein $A_1$=—(CH$_2$)$_q$— where q=0 or 1;

$Y_1$=H or C$_{1-8}$ alkyl when $Z_1$=Cl, Br, or I and $Y_1$=Cl, Br, or I when $Z_1$=H or C$_{1-8}$ alkyl; and $R_{21}$, $R_{22}$, $R_{23}$=H, C$_{1-8}$ alkyl, C$_{3-8}$ cycloalkyl, C$_{2-8}$ alkenyl, or C$_{2-8}$ alkynyl.

2. The compound of claim 1, where q=0.

3. The compound of claim 2, wherein $Y_1$=H or C$_{1-8}$ alkyl and $Z_1$=Cl, Br or I.

4. The compound of claim 2, wherein $Y_1$=Cl, Br or I and $Z_1$=H or C$_{1-8}$ alkyl.

5. The compound of claim 1 wherein q=1.

6. The compound of claim 5, wherein $Y_1$=H or C$_{1-8}$ alkyl and $Z_1$=Cl, Br or I.

7. The compound of claim 5, wherein $Y_1$=Cl, Br or I and $Z_1$=H or C$_{1-8}$ alkyl.

* * * * *